United States Patent [19]

Missel et al.

[11] Patent Number: 5,212,162
[45] Date of Patent: May 18, 1993

[54] USE OF COMBINATIONS GELLING POLYSACCHARIDES AND FINELY DIVIDED DRUG CARRIER SUBSTRATES IN TOPICAL OPHTHALMIC COMPOSITIONS

[75] Inventors: Paul J. T. Missel; John C. Lang, both of Arlington; Rajni Jani, Fort Worth, all of Tex.

[73] Assignee: Alcon Laboratories, Inc.

[21] Appl. No.: 857,673

[22] Filed: Mar. 25, 1992

Related U.S. Application Data

[63] Continuation of Ser. No. 676,146, Mar. 27, 1991, abandoned.

[51] Int. Cl.$^5$ .................. A61K 31/715; A61K 31/70
[52] U.S. Cl. ........................................ 514/54; 514/57; 514/913; 514/912; 536/1.11; 536/114; 536/123.1; 424/427
[58] Field of Search ............... 514/54, 57, 912, 913; 536/1.1; 424/427

[56] References Cited

U.S. PATENT DOCUMENTS

| | | | |
|---|---|---|---|
| 4,014,335 | 3/1977 | Arnold | 424/427 |
| 4,136,173 | 1/1979 | Pramoda et al. | 424/177 |
| 4,136,177 | 1/1979 | Lin et al. | 424/211 |
| 4,136,178 | 1/1979 | Lin et al. | 424/211 |
| 4,505,923 | 3/1985 | Hoffman, Jr. et al. | 514/912 |
| 4,861,760 | 8/1989 | Mazuel et al. | 536/1.1 |
| 4,911,920 | 3/1990 | Jani et al. | 514/913 |
| 4,931,279 | 6/1990 | Bawa et al. | 424/427 |
| 4,983,585 | 1/1991 | Pennell et al. | 514/57 |

OTHER PUBLICATIONS

Maren et al., *Exp. Eye Res.*, 36: 457–480 (1983).
Maren et al., *Exp. Eye Res.*, 50: 27–36 (1990).
Harris, P. (ed), *Food Gels*, New York: Elsevier Applied Science, 1990, Ch. 3 (pp. 79–119) and Ch. 6 (pp. 201–232).
*McGraw-Hill Dictionary of Scientific and Technical Terms*, Third Edition, New York: 1984 p. 1640.

*Primary Examiner*—Michael G. Wityshyn
*Assistant Examiner*—Louise N. Leary
*Attorney, Agent, or Firm*—Julie J. L. Cheng; Sally S. Yeager

[57] ABSTRACT

Ophthalmic compositions comprising combinations of gelling polysaccharides and finely-divided drug carrier substrates which become relatively more viscous on contact with the eye are disclosed. These ophthalmic compositions are both comfortable and long-lasting Ophthalmic compositions further comprising a pharmaceutically active drug are also disclosed, as are methods of use.

27 Claims, No Drawings

USE OF COMBINATIONS GELLING POLYSACCHARIDES AND FINELY DIVIDED DRUG CARRIER SUBSTRATES IN TOPICAL OPHTHALMIC COMPOSITIONS

This application is a continuation of Application Ser. No. 07/676,146, filed Mar. 27, 1991, now abandoned.

BACKGROUND OF THE INVENTION

1. Field of the Invention

The present invention relates to the use of adjuvants in topical ophthalmic compositions. In particular, this invention relates to the use of a combination of gelling polysaccharides and finely-divided drug carrier substrates in the compositions and a method for the controlled administration of a drug to patients wherein the compositions are administered as liquids which thicken to form gels upon instillation into the eye.

2. Description of the Related Art

There have been a multiplicity of liquids, ointments, gels and inserts used as vehicles in topical ophthalmic formulations. Liquid compositions for drop-wise instillation to the eye provide for easy formulation, but do not provide an accurate dosage amount, as portions of the liquid are often blinked away during their administration. Ointments and gels, while providing more accurate administration, often interfere with a patient's vision. Ocular inserts, both bioerodible and non-bioerodible, are also available and allow for less frequent administration of drug; however, these inserts require complex and detailed preparation. An additional problem with the non-bioerodible inserts is that they must be removed after use.

U.S. Pat. Nos. 4,136,173 (Pramoda, et al.), 4,136,177 (Lin, et al.) and 4,136,178 (Lin, et al.) disclose the use of therapeutic compositions containing xanthan gum and locust bean gum which are delivered in liquid form and which gel upon instillation. In these three patents, the mechanism for transition from liquid to gel is due to a change in pH.

U.S. Pat. No. 4,861,760 (Mazuel, et al.) discloses ophthalmological compositions containing gellan gum which are administered as non-gelled liquids and which gel upon instillation due to the change in ionic strength.

Commonly assigned U.S. patent application Ser. No. 07/641,214, filed on Jan. 15, 1991, discloses ophthalmic formulations containing carrageenans and furcellarans (hereinafter collectively referred to as "carrageenans") which are administered as partially gelled liquids which gel upon instillation into the eye.

SUMMARY OF THE INVENTION

The present invention is directed to topical ophthalmic compositions comprising combinations of gelling polysaccharides (defined below) and finely-divided drug carrier substrates (hereinafter "DCS" and defined below) to provide comfort and sustained release of drug to the eye, as well as methods for their use. In addition, the compositions without drug can be administered in order to lubricate the eye or to supplement tears in the treatment of, for example, dry eye. The compositions are administered as liquids or partially gelled liquids (hereinafter collectively referred to as "liquids") which thicken to form gels upon instillation into the eye.

DETAILED DESCRIPTION OF THE INVENTION

As used herein, the term "gelling polysaccharide" means a polysaccharide capable of a reversible liquid-to-gel transition based on a change in ionic strength or pH. Such factors as a change in temperature, amount and type of DCS, and characteristics and concentrations of drugs or other adjuvants may also affect the ability of the gelling polysaccharides to undergo a liquid-to-gel transition. Suitable gelling polysaccharides include, but are not limited to: xanthan gum, locust bean gum, gellan gum, carrageenans and combinations thereof. These gelling polysaccharides are discussed in detail in U.S. Pat. Nos. 4,136,173, 4,136,177, 4,136,178, 4,861,760, and U.S. patent application Ser. No. 07/641,214, respectively. The contents of these patents and patent applications relating to the gelling polysaccharides cited above are hereby incorporated by reference herein.

The preferred gelling polysaccharides of the present invention are the carrageenans, especially carrageenans with not more than 1.0 sulfate moiety per disaccharide unit such as eucheuma carrageenan and furcellaran. These provide both great contrast in the ratio of gel elastic modulus to viscosity over the temperature ranges of interest, as explained below, as well as limited response to drug counter-ions, especially as to their influence on gellation.

The DCS component of the present compositions is added to provide an additional means of controlling release, as well as to prevent the stinging which often occurs with the topical administration of certain drugs, such as betaxolol. As used herein, the term "finely-divided drug carrier substrate" (or "DCS") means finely-divided solids, colloidal particles, or soluble polymers and/or polyelectrolytes which are capable of selective adsorption or binding with drug molecules. Examples of DCS include, but are not limited to: finely divided silica, such as fumed silica, silicates and bentonites; ion exchange resins, which can be anionic, cationic or non-ionic in nature; and soluble polymers, such as, alginic acid, pectin, soluble carrageenans, carbopol, and polystyrene sulfonic acid. Preferred DCS are the ion exchange resins. Some resins which are used in chromatography make ideal DCS for binding drugs in the compositions of the present invention.

Ion exchange resins are typically in the form of beads which may be either porous or non-porous. Porous beads can be advantageous because they provide more surface area for the placement of functional groups, which lead to increased drug binding and improved sustained release.

Functional groups which may be added to the resin beads or polymers include acids, bases or neutral hydrophobic or hydrophilic groups to influence the binding of the drug. Specific functional groups may include, but are not limited to: sulfonic acid, carboxylic acid, phosphoric acid, aromatic groups such as phenyl or pyridinium, alkyl carbon chains, polyethylene oxide, polypropylene oxide, polypropylene oxide, carboxymethyl, sulfopropyl, polyglycol and combinations thereof. The choice of functional group will depend on the drugs to be delivered, especially their charge at the pH of the composition. For example, drugs with a positive charge at the desired composition pH will typically be formulated with resins having cationic functional groups at the composition pH.

Cationic exchange resins are characterized as either strongly acidic, such as those having sulfonic acid functionality, or weakly acidic, such as those having carboxylic acid functionality. Anionic exchange resins are characterized as either strongly basic, containing, for example, quaternary ammonium functionalities, or weakly basic, containing, for example, amines. Non-ionic resins may have any of a variety of functionalities whose charges offset each other (i.e., zwitterions), resulting in a neutral resin, or they may be comprised of non-ionic polymers having any of a variety of hydrophilic functional groups.

The choice of resin functional group density (hereinafter "charge density") will also depend on the nature of the drug to be delivered. For example, drugs having multiple sites capable of binding or adhering to a resin (multiple resin binding sites) such as tobramycin, are strongly attracted to resins having relatively high charge densities, such as Amberlite. Such combinations would not necessarily be desirable, since the resin-drug affinity would be so great that little or no drug would be available to the eye in a reasonable time period. Therefore, drugs having multiple resin binding sites are preferably combined with resins having relatively low charge densities, such as carboxymethyl Sephadex. This will provide for a composition wherein the drug is available to the eye, but over a period of time. On the other hand, other drugs which do not have multiple resin binding sites are preferably combined with resins having a relatively high charge density in order to achieve a sustained release.

The size of the DCS can be important, both with respect to mode of action and comfort. The average particle size of the typical commercially available form of the DCS material of choice, an ion exchange resin, is about 40 to about 150 microns. Such particles are most conveniently reduced to a particle size range of about 1.0 to about 25.0 microns, preferably between about 1.0 and 10.0 microns, by ball milling, according to known techniques. In the alternative, small particles may be synthesized in the optimal size range of 3–7 microns. Although this procedure can be more expensive, it is superior in providing a more uniform and narrow distribution of sizes in the preferred range.

The DCS component is present in the compositions of the present invention at a level in the range of about 0.05 to about 10.0% by weight. For particulate DCS, the average particle size diameter ranges from 1 to 20 microns. The amount of DCS and its characteristics (e.g., amount of cross-linking, particle size) may be varied in order to produce the desired time-release profile for the chosen drug. A long time-release profile, desirable for a drug having a short biological half-life, such as apraclonidine, may be achieved by using a large excess of DCS (i.e., the number of DCS binding/exchange sites is several times that of the drug(s) being delivered). An intermediate release profile, suggested for a drug such as pilocarpine, with a reasonably good half-life (4 hours), may be obtained by using a small excess of DCS or no excess DCS (i.e., the number of DCS binding sites is equivalent to that of the drug(s) being delivered). For drugs which have serious side effects, such as betaxolol, a preferred release profile is usually a rapid initial release spike, to release an amount of drug effective to cross the therapeutic threshold, followed by a sustained release tail, to maintain the therapeutic effect but to reduce or eliminate side effects. This may be achieved by using an excess of drug (as compared to the number of DCS binding sites).

DCS materials which can be used on the composition of the present invention may include, but are not limited to: fumed silica, e.g., Cab-O-Sil (Cabot Corporation, Boyertown, Penna.); silicates, e.g., Veegums (R. T. Vanderbilt, Norwalk, Conn.), Gelwhite (ECC American, Inc., Dover, Ohio); bentonites, e.g., bentonite (native hydrated colloidal aluminum silicate clay), Claytone (ECC American, Inc., Dover, Ohio), Macaloid (NL Chemicals, Hightstown, N.J.), Bentone EW (NL chemical, Hightstown, N.J.); polystyrene/ divinylbenzene, e.g. Amberlite IRP-69 (Rohm & Haas, Philadelphia, Penna.) and RCX-20 (Hamilton, Reno, Nev.); polymethacrylic acid, e.g. Amberlite IRP-64 (Rohm & Haas); hydroxymethylmethacrylate (HEMA), e.g. HEMA-IEC BIO 1000 SB (Alltech Associates, Deerfield, Ill.); cross-linked dextran, e.g. Sephadex (Dow Chemicals, Midland, Mich.); and alginic acid.

The compositions of the present invention may be formulated in many ways, for example 1) a liquid formulation, wherein the composition is a low viscosity liquid which becomes a high viscosity liquid or a gel upon instillation in the eye; 2) a stiff gel formulation, wherein the composition is a weak gel which becomes a stiffer gel in the eye; and 3) a thixotropic formulation, wherein the composition is a viscous liquid when shaken and a gel when left standing for a period of time.

The different types of formulations discussed above exhibit different physical characteristics. For the sake of clarity and for ease of a reference in the discussion below, "pre-dosed" refers to a formulation's characteristics before topical administration to the eye and "post-dosed" refers to a formulation's characteristics after administration into the eye.

The liquid formulations have a pre-dosed viscosity in the range of about 1 to about 500 centipoise (cps), with about 1 to about 200 cps preferred, and about 1 to about 100 cps most preferred. If the liquid formulations do not form a gel in the eye, but simply become more viscous, the post-dosed viscosity will be greater than about 50 cps, preferably greater than about 150 cps, and most preferably greater than about 300 cps. If the liquid formulations do form a gel in the eye, the gel will have a modulus of elasticity (Young's modulus) in the range of about $1 \times 10^4$ to about $5 \times 10^5$ dynes/cm$^2$, with about $2 \times 10^4$ to about $5 \times 10^5$ dynes/cm$^2$ preferred and about $5 \times 10^4$ to about $5 \times 10^5$ dynes/cm$^2$ most preferred.

The stiff gel formulations have a pre-dosed modulus of elasticity in the range of about $1 \times 10^4$ to about $3 \times 10^5$ dynes/cm$^2$, with about $2 \times 10^4$ to about $2 \times 10^5$ dynes/cm$^2$ preferred and about $5 \times 10^4$ to about $1 \times 10^5$ dynes/cm$^2$ most preferred. The post-dosed stiff formulations are gels and will have a modulus of elasticity in the range of about $1 \times 10^4$ to about $2 \times 10^6$ dynes/cm$^2$, with $1 \times 10^5$ to about $7 \times 10^5$ dynes/cm$^2$ preferred and about $2 \times 10^5$ to about $5 \times 10^5$ dynes/cm$^2$ most preferred.

The thixotropic formulations, when shaken, have a pre-dosed viscosity in the range of about 1 to about 5000 cps, with about 50 to about 1000 cps preferred and about 200 to about 500 cps most preferred. The pre-dosed gel forms of the thixotropic formulations have a modulus of elasticity in the range of about $1 \times 10^4$ to about $2 \times 10^5$ dynes/cm$^2$, with about $2 \times 10^4$ to about $1 \times 10^5$ dynes/cm$^2$ preferred and about $3 \times 10^4$ to about $7 \times 10^4$ dynes/cm$^2$ most preferred. The post-dosed gels will have a modulus of elasticity in the range of about $1 \times 10^4$ to about $2 \times 10^6$ dynes/cm$^2$, with about $2 \times 10^4$ to about $1\times10^5$ dynes/cm$^2$ preferred and about $3\times10^4$ to about $7\times10^4$ dynes/cm$^2$ most preferred.

Suitable ophthalmic agents ("drugs") which can be included in the compositions of the present invention and administered via the method of the present invention include, but are not limited to: glaucoma agents, such as betaxolol, pilocarpine and carbonic anhydrase inhibitors; dopaminergic antagonists; post-surgical antihypertensive agents, such as a para-amino clonidine (apraclonidine); anti-infectives, such as ciprofloxacin; non-steroidal and steroidal anti-inflammatories, such as suprofen, ketorolac and tetrahydrocortisol; prostaglandins; proteins; growth factors, such as EGF; and anti-allergics. Compositions of the present invention may also include combinations of ophthalmic agents. In a formulation without the use of ophthalmic agents, the present invention may also serve to supplement tears in the prevention or treatment of dry eye.

The compositions of the present invention can include other components, for example, ophthalmically acceptable buffers, preservatives, and tonicity agents.

In general, for water-soluble drugs, the compositions of the present invention are formulated such that the DCS is added to the solution prior to the addition of drug (if any) and the gelling polysaccharide is added last, after all the other ingredients have been mixed. Where the drug to be included in the compositions of the present invention has a low solubility, it is preferred that the drug be added last, that is, after the addition of the gelling polysaccharide. In certain cases, it may also be preferred that the drug be separately sterilized (e.g., with radiation) and aseptically added to the other ingredients, which have been autoclaved according to the sterilization procedure described below.

Sterilization of the compositions can be accomplished by autoclaving. It is well known that an order of magnitude reduction in sterilization time is achieved for every 10° C. rise in sterilization temperature. As the gelling polysaccharides tend to decompose and caramelize when heated, sterilization at higher temperatures with lower sterilization time is generally preferred. The preferred temperature range is greater than about 130° C., with a sterilization time of less than about 3 minutes when the pH of the composition is more than about 6. In the alternative, aseptic combinations of drug and gelling polysaccharide can be utilized when the hydration of resin results in chemical instability of drug or of the drug/DCS complex. In those instances where the final pH of the composition is less than 6, it is preferred that sterilization take place at pH close to 7.4, then to adjust the pH by aseptic means to its final value.

The following examples are presented to illustrate further various aspects of the present invention, but are not intended to limit the scope of the invention in any respect.

EXAMPLE 1

The following are examples of stiff gel formulations:

| Ingredients | Percent by weight/volume | | | | | | | | | | |
|---|---|---|---|---|---|---|---|---|---|---|---|
| | A | B | C | D | E | F | G | H | I | J | K |
| Eucheuma Carrageenan[1] | — | 2.0 | 2.0 | 2.0 | 2.0 | 2.0 | 2.0 | 2.0 | 2.0 | 2.0 | — |
| Furcellaran[2] | 0.6 | — | — | — | — | — | — | — | — | — | 0.6 |
| Na$_2$HPO$_4$ | 0.1 | 0.1 | 0.1 | 0.1 | 0.1 | 0.1 | 0.1 | 0.1 | 0.1 | — | — |
| Mannitol | 3.5 | 3.5 | 3.5 | 3.5 | 3.5 | 3.5 | 3.5 | 3.5 | 3.5 | 3.5 | 3.5 |
| Acid Amberlite | 5.0 | 5.0 | 3.0 | — | — | — | — | — | 5.0 | — | — |
| RCX-20 | — | — | — | 5.0 | — | — | — | — | — | — | — |
| Cellulose Phosphate | — | — | — | — | 5.0 | — | — | — | — | — | — |
| Carboxymethyl Sephadex | — | — | — | — | — | 4.0 | — | — | — | — | — |
| Sulfopropyl Sephadex | — | — | — | — | — | — | 7.2 | — | — | — | — |
| Amberlite CG400 | — | — | — | — | — | — | — | 5.0 | — | — | — |
| Bentonite | — | — | — | — | — | — | — | — | — | 2.0 | — |
| Cab-O-Sil | — | — | — | — | — | — | — | — | — | — | 1.0 |
| S-Betaxolol (free base) | — | 0.5 | — | — | — | — | — | — | — | — | — |
| Apraclondine | — | — | 1.0 | — | — | — | — | — | — | 1.0 | — |
| Pilocarpine | — | — | — | 1.0 | — | — | — | — | — | — | — |
| Tobramycin | — | — | — | — | 2.0 | 2.0 | 2.0 | 2.0 | — | — | — |
| Suprofen | — | — | — | — | — | — | — | — | 1.0 | — | — |
| Water | QS | QS | QS | QS | QS | QS | QS | QS | QS | QS | QS |

[1]Extracted from *Eucheuma gelatinae*.
[2]Extracted from *Furcellaria fastigata*.

Preparation of Formulation B

The following procedure was utilized to prepare a 50 milliliter (ml) batch of Formulation B.

Approximately 30 ml of water (about 2/3 of the final volume), 0.051 grams (g) of Na$_2$HPO$_4$ (0.1% w/v) and 1.750 g of mannitol (3/5% w/v) were added to a beaker equipped with a magnetic stir bar. The mixture was stirred until the ingredients were dissolved, then 8.357 g of rinsed Acid Amberlite (corresponding to 2.5 g dry weight) was added and the mixture stirred for another 15 minutes (min), until the Amberlite was uniformly mixed; that is, until there were no lumps. The pH of the mixture was raised from 1.96 to 2.51 by the addition of 10N NaOH. After the pH adjustment, 0.24 g of S-betaxolol (free base) was added and mixture stirred approximately ¼ hour without adjusting pH. The pH of the mixture was then adjusted to 3.34 by addition of 1N NaOH. The mixture was stirred overnight (at least 12 hours) to ensure that the S-betaxolol was adequately bound to the Acid Amberlite. The pH of the mixture was then raised to 7.40 with 10N NaOH and water added to bring the final volume to 50 ml. The mixture was then heated to 75° C. and 1.000 g of eucheuma carrageenan (2%) added. The mixture was then stirred, heated, and maintained at 90° C. for a half hour. When the mixture was removed from the heat, the osmolality was checked. The final osmolality was 308 milliOsmolal (mOsm).

The mixture was sterilized in an autoclave at 130° C. for 3 minutes in containers having radii no greater than 1 centimeter (cm). After sterilization, the containers were removed and allowed to air cool to room temperature.

EXAMPLE 2

The following are examples of thixotripic gel formulations:

| Ingredients | Percent by weight/volume | | | | | | | | | |
|---|---|---|---|---|---|---|---|---|---|---|
| | A | B | C | D | E | F | G | H | I | J |
| Eucheuma Carrageenan | — | 0.6 | 0.6 | 0.6 | 0.6 | 0.6 | 0.6 | 0.6 | 0.6 | 0.6 |
| Gellan Gum | 0.6 | — | — | — | — | — | — | — | — | — |
| Na$_2$HPO$_4$ | 0.1 | 0.1 | 0.1 | 0.1 | 0.1 | 0.1 | 0.1 | 0.1 | 0.1 | 0.1 |
| Mannitol | 3.5 | 3.5 | 3.5 | 3.5 | 3.5 | 3.5 | 3.5 | 3.5 | 3.5 | 3.5 |

-continued

| Ingredients | \multicolumn{10}{c}{Percent by weight/volume} | | | | | | | | | |
|---|---|---|---|---|---|---|---|---|---|---|
| | A | B | C | D | E | F | G | H | I | J |
| Acid Amberlite | 5.0 | 5.0 | 3.0 | — | — | — | — | — | 5.0 | 5.0 |
| RCX-20 | — | — | — | 5.0 | — | — | — | — | — | — |
| Cellulose Phosphate | — | — | — | — | 5.0 | — | — | — | — | — |
| Carboxymethyl Sephadex | — | — | — | — | — | 4.0 | — | — | — | — |
| Sulfopropyl Sephadex | — | — | — | — | — | — | 7.2 | — | — | — |
| Amberlite CG400 | — | — | — | — | — | — | — | 5.0 | — | — |
| S-Betaxolol (free base) | — | 0.5 | — | — | — | — | — | — | — | — |
| Apraclonidine | — | — | 1.0 | — | — | — | — | — | — | — |
| Pilocarpine | — | — | — | 1.0 | — | — | — | — | — | — |
| Tobramycin | — | — | — | — | 2.0 | 2.0 | — | 2.0 | 2.0 | — |
| Suprofen | — | — | — | — | — | — | — | — | 1.0 | — |
| ALO4414A[1] | — | — | — | — | — | — | — | — | — | 2.0 |
| Water | QS | QS | QS | QS | QS | QS | QS | QS | QS | QS |

[1] (+)-4-Ethylamino-2,3-dihydro-4H-2-methylthieno[3,2-e]-1,2-thiazine-6-sulfonamide-1,1-dioxide HCl.

The compounding procedure for these formulations are similar to the procedure detailed in Example 1, above.

EXAMPLE 3

The following are examples of liquid formulations:

| Ingredients | \multicolumn{8}{c}{Percent by weight/volume} | | | | | | | |
|---|---|---|---|---|---|---|---|---|
| | A | B | C | D | E | F | G | H |
| Eucheuma Carrageenan | 0.3 | — | 0.3 | — | 0.3 | 0.3 | — | — |
| Kappa Carrageenan[1] | — | 0.5 | — | — | — | — | 0.5 | — |
| Furcellaran | — | — | — | 0.3 | — | — | — | 0.3 |
| Na$_2$HPO$_4$ | 0.1 | 0.1 | 0.1 | 0.1 | 0.1 | — | 0.1 | — |
| Mannitol | 3.5 | 3.5 | 3.5 | 3.5 | 3.5 | 3.5 | 3.5 | 3.5 |
| Acid Amberlite | 5.0 | 5.0 | 5.0 | 5.0 | 5.0 | — | — | — |
| Claytone | — | — | — | — | — | 2.0 | — | — |
| Gelwhite | — | — | — | — | — | 2.0 | — | — |
| Bentonite | — | — | — | — | — | — | — | 2.0 |
| S-Betexolol (free-base) | 0.5 | — | — | — | — | — | 0.5 | — |
| Pilocarpine | — | — | — | — | 1.0 | 1.0 | — | — |
| ALO4414A | — | — | 2.0 | — | — | — | — | — |
| Water | QS | QS | QS | QS | QS | QS | QS | QS |

[1] Extracted from *Eucheuma cottonii*.

Compounding procedures are similar to the procedure detailed in Example 1, above.

What is claimed is:

1. A topical ophthalmic composition comprising a gelling polysaccharide and a finely-divided drug carrier substrate, wherein the concentration of said gelling polysaccharide allows the composition to be administrable as a drop which gels upon instillation to the eye.

2. The composition of claim 1 wherein the finely-divided drug carrier substrate is an ion exchange resin.

3. The composition of claim 1 wherein the gelling polysaccharide concentration is between 0.1% and 3.0% by weight/volume and the concentration of the finely-divided drug carrier substrate is between 0.05% and 10.0% by weight/volume.

4. The composition of claim 1 wherein the gelling polysaccharide is selected from the group consisting of xanthan gum, locust beam gum, gellan gum, and carrageenan.

5. The composition of claim 4 wherein the gelling polysaccharide is gellan gum.

6. The composition of claim 4 wherein the gelling polysaccharide is a carrageenan having not more than 1.0 sulfate moiety per disaccharide repeating unit.

7. The composition of claim 6 wherein said carrageenan is eucheuma carrageenan.

8. The composition of claim 6 wherein said carrageenan is furcellaran.

9. The composition of claim 1 wherein the pre-dosed viscosity thereof is between 1 and 500 cps and the post-dosed viscosity is greater than 50 cps.

10. The composition of claim 1 wherein the pre-dosed viscosity thereof is between 1 and 500 cps and the post-dosed gel has a modulus of elasticity between $1 \times 10^4$ and $5 \times 10^5$ dynes/cm$^2$.

11. The composition of claim 1 wherein the pre-dosed modulus of elasticity thereof is between $1 \times 10^4$ and $3 \times 10^5$ dynes/cm$^2$ and the post-dosed modulus of elasticity thereof is between $1 \times 10^4$ and $2 \times 10^6$ dynes/cm$^2$.

12. The composition of claim 1 wherein the composition is thixotropic, having a pre-dosed modulus of elasticity between $1 \times 10^4$ and $2 \times 10^5$ dynes/cm$^2$ and, after shaking, a pre-dosed viscosity between 1 and 5000 cps and having a post-dosed modulus of elasticity between $1 \times 10^4$ and $2 \times 10^6$ dynes/cm$^2$.

13. The composition of claim 1 further comprising an ophthalmic agent.

14. The composition of claim 13 wherein the ophthalmic agent is para-amino clonidine.

15. The composition of claim 13 wherein the ophthalmic agent is a carbonic anhydrase inhibitor.

16. The composition of claim 15 wherein the carbonic anhydrase inhibitor is (+)-4-ethylamino-2,3-dihydro-4H-2-methylthieno-[3,2-e]1,2-thiazine-6-sulfonamide-1,1-dioxide or a pharmaceutically acceptable salt thereof.

17. A method of delivering an ophthalmic agent to the eye which comprises topically administering a composition comprising: an ophthalmic agent, a gelling polysaccharide, and a finely-divided drug carrier substrate, wherein the concentration of said gelling polysaccharide allows the composition to be administrable as a drop which gels upon instillation to the eye.

18. The method of claim 17 wherein the finely-divided drug carrier substrate is an ion exchange resin.

19. The method of claim 17 wherein the gelling polysaccharide concentration is between 0.1% and 3.0% by weight/volume and the finely-divided drug carrier substrate concentration is between 0.05% and 10.0% by weight/volume.

20. The method of claim 17 wherein the gelling polysaccharide is selected from the group consisting of xanthan gum, locust bean gum, gellan gum, and carrageenan.

21. The method of claim 20 wherein the gelling polysaccharide is gellan gum.

22. The method of claim 20 wherein the gelling polysaccharide is a carrageenan having not more than 1.0 sulfate moiety per disaccharide repeating unit.

23. The method of claim 22 wherein said carrageenan is eucheuma carrageenan.

24. The method of claim 22 wherein said carrageenan is furcellaran.

25. The method of claim 17 wherein the ophthalmic agent is para-amino clonidine.

26. The method of claim 17 wherein the ophthalmic agent is a carbonic anhydrase inhibitor.

27. The method of claim 26 wherein the carbonic anhydrase inhibitor is (+)-4-ethylamino-2,3-dihydro-4H-2-methylthieno-[3,2-e]1,2-thiazine-6-sulfonamide-1,1-dioxide or a pharmaceutically acceptable salt thereof.

* * * * *